United States Patent
Peters et al.

(10) Patent No.: US 7,989,470 B2
(45) Date of Patent: Aug. 2, 2011

(54) 3,8-SUBSTITUTED 8-AZA-BICYCLO[3.2.1]OCTANE DERIVATIVES AND THEIR USE AS MONOAMINE NEUROTRANSMITTER RE-UPTAKE INHIBITORS

(75) Inventors: Dan Peters, Malmo (SE); Bjarne H. Dahl, Lynge (DK); Gunnar M. Olsen, Smorum (DK); Elsebet Ostergaard Nielsen, Kobenhavn K (DK); Jorgen Scheel-Kruger, Glostrup (DK); John Paul Redrobe, Kobenhavn K (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 12/727,972

(22) Filed: Mar. 19, 2010

(65) Prior Publication Data

US 2010/0190821 A1    Jul. 29, 2010

Related U.S. Application Data

(62) Division of application No. 11/794,365, filed as application No. PCT/EP2006/050143 on Jan. 11, 2006, now Pat. No. 7,713,990.

(60) Provisional application No. 60/643,590, filed on Jan. 14, 2005.

(30) Foreign Application Priority Data

Jan. 13, 2005   (DK) ................. 2005 00068

(51) Int. Cl.
    A61K 31/46    (2006.01)
    C07D 451/02    (2006.01)

(52) U.S. Cl. ........................ 514/304; 546/124

(58) Field of Classification Search ........ 514/304; 546/124
    See application file for complete search history.

(56) References Cited

U.S. PATENT DOCUMENTS

| | | | |
|---|---|---|---|
| 3,396,168 A | 8/1968 | Corts et al. | |
| 3,657,253 A | 4/1972 | Helsley | |
| 4,861,889 A | 8/1989 | Helsley et al. | |
| 4,916,139 A | 4/1990 | Helsley | |
| 5,185,343 A | 2/1993 | Chenard | |
| 5,272,160 A | 12/1993 | Chenard | |
| 5,306,723 A | 4/1994 | Chenard | |
| 5,338,754 A | 8/1994 | Chenard | |
| 5,391,742 A | 2/1995 | Chenard | |
| 5,498,610 A | 3/1996 | Chenard | |
| 5,527,912 A | 6/1996 | Chenard | |
| 5,710,168 A | 1/1998 | Chenard | |
| 6,046,213 A | 4/2000 | Chenard | |
| 6,258,827 B1 | 7/2001 | Chenard | |
| 2004/0063688 A1 | 4/2004 | Blumberg | |

FOREIGN PATENT DOCUMENTS

| | | |
|---|---|---|
| EP | 0 333 026 A1 | 9/1989 |
| EP | 1 731 518 A1 | 12/2006 |
| JP | 4-54181 A | 2/1992 |
| WO | WO-84/01151 A1 | 3/1984 |
| WO | WO-03/062235 A1 | 7/2003 |
| WO | WO-2004/009588 A1 | 1/2004 |
| WO | WO-2004/113334 A1 | 12/2004 |
| WO | WO-2005/095380 A1 | 10/2005 |

OTHER PUBLICATIONS

Liegeois et al., "New Pyridobenzodiazepine Derivates: Modifications of the Basic Side Chain Differentially Modulate Binding to Dopamine (D4.2, D2L) and Serotonin (5-HT2A) Receptors," Journal of Medicinal Chemistry, vol. 45, CODEN: JMCMAR; ISSN: 0022-2623, 2002, XP009065020, pp. 5136-5149.

Boswell et al., "Synthesis of some N-carboxylic acid derivatives of 3-phenoxypyrrolidines, 4-phenoxypiperidines, and 3-phenoxynortropanes with muscle relaxant and anticonvulsant activities," Journal of Medicinal Chemistry, vol. 17, CODEN: JMCMAR; ISSN: 0022-2623, 1974, XP009065021, pp. 1000-1008.

*Primary Examiner* — Rebecca L Anderson
*Assistant Examiner* — Samantha L. Shterengarts
(74) *Attorney, Agent, or Firm* — Birch, Stewart, Kolasch and Birch, LLP

(57) ABSTRACT

This invention relates to novel 8-aza-bicyclo[3.2.1]octane derivatives useful as monoamine neurotransmitter re-uptake inhibitors.

In other aspects the invention relates to the use of these compounds in a method for therapy and to pharmaceutical compositions comprising the compounds of the invention.

12 Claims, No Drawings

3,8-SUBSTITUTED 8-AZA-BICYCLO[3.2.1]OCTANE DERIVATIVES AND THEIR USE AS MONOAMINE NEUROTRANSMITTER RE-UPTAKE INHIBITORS

This application is a Divisional of co-pending application Ser. No. 11/794,365 filed on Jun. 28, 2007, and for which priority is claimed under 35 U.S.C. §120; application Ser. No. 11/794,365 is the national phase of PCT International Application No. PCT/EP2006/050143 filed on Jan. 11, 2006 under 35 U.S.C. §371; Application No. PCT EP2006/050143 claims priority under 35 U.S.C. §119 to Application No. 60/643,590 filed on Jul. 14, 2005; and Application No. 60/643,590 claims priority to PA 2005/00068 filed in Denmark on Jan. 13, 2005; the entire contents of all of the above applications are herein incorporated by reference.

TECHNICAL FIELD

This invention relates to novel 8-aza-bicyclo[3.2.1]octane derivatives useful as monoamine neurotransmitter re-uptake inhibitors.

In other aspects the invention relates to the use of these compounds in a method for therapy and to pharmaceutical compositions comprising the compounds of the invention.

BACKGROUND ART

Serotonin Selective Reuptake Inhibitors (SSRIs) currently provide efficacy in the treatment of several CNS disorders, including depression and panic disorder. SSRIs are generally perceived by psychiatrists and primary care physicians as effective, well-tolerated and easily administered. However, they are associated with a number of undesirable features.

Thus, there is still a strong need for compounds with an optimised pharmacological profile as regards the activity on reuptake of the monoamine neurotransmitters serotonin, dopamine and noradrenaline, such as the ratio of the serotonin reuptake versus the noradrenaline and dopamine reuptake activity.

SUMMARY OF THE INVENTION

In its first aspect, the invention provides a compound of Formula I:

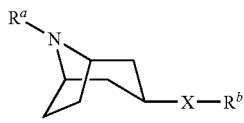

(I)

or any of its isomers or any mixture of its isomers, or a pharmaceutically acceptable salt thereof,
wherein $R^a$, $R^b$ and X are as defined below.

In its second aspect, the invention provides a pharmaceutical composition, comprising a therapeutically effective amount of a compound of the invention, or any of its isomers or any mixture of its isomers, or a pharmaceutically acceptable salt thereof, together with at least one pharmaceutically acceptable carrier, excipient or diluent.

In a further aspect, the invention provides the use of a compound of the invention, or any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to inhibition of monoamine neurotransmitter re-uptake in the central nervous system.

In a still further aspect, the invention relates to a method for treatment, prevention or alleviation of a disease or a disorder or a condition of a living animal body, including a human, which disorder, disease or condition is responsive to responsive to inhibition of monoamine neurotransmitter re-uptake in the central nervous system, which method comprises the step of administering to such a living animal body in need thereof a therapeutically effective amount of a compound of the invention, or any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION 8-aza-bicyclo[3.2.1]octane derivatives
In its first aspect the present invention provides compounds of formula I:

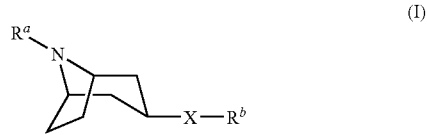

(I)

or any of its isomers or any mixture of its isomers,
or a pharmaceutically acceptable salt thereof,
wherein
$R^a$ represents —$(R^c)_n$—$R^d$, —$(R^c)_n$—C(=O)R', —$(R^c)_n$—C(=O)OR', —$(R^c)_n$—C(=S)NR'R" or —$(R^c)_n$—C(=O)NR'R";
  wherein $R^c$ represents alkyl;
  n is 0 or 1;
  $R^d$ represents aryl or heteroaryl;
    which aryl or heteroaryl is optionally substituted with one or more substituents independently selected from the group consisting of:
      halo, trifluoromethyl, trifluoromethoxy, cyano, hydroxy, amino, nitro, oxo, alkoxy, cycloalkoxy, alkyl, cycloalkyl, cycloalkylalkyl, alkenyl and alkynyl;
  R' and R" independent of each other represent hydrogen, alkyl, aryl or heteroaryl;
    which aryl or heteroaryl is optionally substituted with one or more substituents independently selected from the group consisting of:
      halo, trifluoromethyl, trifluoromethoxy, cyano, hydroxy, amino, nitro, oxo, alkoxy, cycloalkoxy, alkyl, cycloalkyl, cycloalkylalkyl, alkenyl and alkynyl;
X represents —O—, —S— or —$NR^e$—;
  wherein $R^e$ represents hydrogen, alkyl, —C(=O)$R^f$ or —$SO_2R^f$;
    wherein $R^f$ represents hydrogen or alkyl;
$R^b$ represents aryl or heteroaryl,
  which aryl or heteroaryl is optionally substituted with one or more substituents independently selected from the group consisting of:

halo, trifluoromethyl, trifluoromethoxy, cyano, hydroxy, amino, nitro, oxo, alkoxy, cycloalkoxy, alkyl, cycloalkyl, cycloalkylalkyl, alkenyl and alkynyl.

In one embodiment, $R^a$ represents —$(R^c)_n$—$R^d$, —$(R^c)_n$—C(=O)R', —$(R^c)_n$—C(=O)OR' or —$(R^c)_n$—C(=O)NR'R''; wherein $R^c$, $R^d$, R', R'' and n are as defined above.

In a second embodiment, $R^a$ represents —$(R^c)_n$—$R^d$; wherein $R^d$ represents optionally substituted phenyl, pyridyl, benzimidazolyl, thiazolyl or tetrazolyl. In a third embodiment, $R^a$ represents —$(R^c)_n$—$R^d$; wherein $R^d$ represents phenyl, pyridyl, benzimidazolyl or tetrazolyl. In a special embodiment, $R^a$ represents phenylalkyl, such as benzyl, phenethyl or 1-phenyl-ethyl. In a further embodiment, $R^a$ represents pyridylalkyl, such as pyridylmethyl, such as pyridin-4-yl-methyl, pyridin-3-yl-methyl, or pyridin-2-yl-methyl. In a still further embodiment, $R^a$ represents benzimidazolyl, such as benzimidazol-2-yl. In a further embodiment, $R^a$ represents tetrazolylalkyl, such as tetrazolylmethyl, such as 1H-tetrazol-5-ylmethyl. In a still further embodiment, $R^a$ represents thiazolylalkyl, such as thiazolylmethyl, such as thiazol-2-ylmethyl. In a further embodiment, $R^a$ represents alkyltetrazolylalkyl, such as methyltetrazolylmethyl, such as 1-methyl-1H-tetrazol-5-ylmethyl.

In a still further embodiment, $R^a$ represents —$(R^c)_n$—C(=O)R'; wherein R' represents hydrogen. In a special embodiment, $R^a$ represents formyl.

In a further embodiment, $R^a$ represents —$(R^c)_n$—C(=O)OR'; wherein R' represents alkyl. In a special embodiment, $R^a$ represents alkoxycarbonylmethyl, such as ethoxycarbonylmethyl.

In a still further embodiment, $R^a$ represents —$(R^c)_n$—C(=O)NR'R''; wherein R' represents hydrogen; and R'' represents hydrogen or phenyl. In a special embodiment, $R^a$ represents aminocarbonylmethyl. In a further embodiment, $R^a$ represents phenyl-aminocarbonyl.

In a further embodiment, $R^a$ represents —$(R^c)_n$—C(=S)NR'R''; wherein R' and R'' represent hydrogen. In a special embodiment, $R^a$ represents aminothiocarbonylmethyl.

In a further embodiment, n is 0. In a still further embodiment, n is 1 and $R_c$ represents —$CH_2$—, —$CH_2$—$CH_2$— or —$C(CH_3)H$—.

In a further embodiment, X represents —O—.

In a still further embodiment, $R^b$ represents aryl or heteroaryl, which aryl or heteroaryl is optionally substituted with one or more substituents independently selected from the group consisting of:
halo, trifluoromethyl, trifluoromethoxy, cyano, oxo, alkyl and alkoxy.

In a further embodiment, $R^b$ represents optionally substituted phenyl, such as phenyl substituted with one or more halo. In a special embodiment, $R^b$ represents dihalophenyl, such as 3,4-dihalophenyl, such as 3,4-dichlorophenyl In a still further embodiment, $R^b$ represents optionally substituted pyridyl, such as pyridyl substituted with one or more halo. In one embodiment, $R^b$ represents halopyridyl, such as halo-pyridin-2-yl. In a special embodiment, $R^b$ represents 5-halo-pyridin2-yl, such as 5-chloro-pyridin-2-yl. In a further embodiment, $R^b$ represents 6-halo-pyridin2-yl, such as 6-bromo-pyridin-2-yl.

In a still further embodiment, $R^b$ represents optionally substituted naphthyl, such as naphthyl substituted with alkoxy, such as methoxy, In one embodiment, $R^b$ represents alkoxy-naphthalen-2-yl, such as 6-alkoxy-naphthalen-2-yl, such as 6-methoxy-naphthalen-2-yl.

In a special embodiment the chemical compound of the invention is
3-(3,4-Dichloro-phenoxy)-8-pyridin-2-ylmethyl-8-aza-bicyclo[3.2.1]octane;
2-[3-(3,4-Dichloro-phenoxy)-8-aza-bicyclo[3.2.1]oct-8-yl]-acetamide;
3-(3,4-Dichloro-phenoxy)-8-aza-bicyclo[3.2.1]octane-8-carboxylic acid phenylamide;
3-(3,4-Dichloro-phenoxy)-8-pyridin-3-ylmethyl-8-aza-bicyclo[3.2.1]octane;
3-(5-Chloro-pyridin-2-yloxy)-8-pyridin-2-ylmethyl-8-aza-bicyclo[3.2.1]octane;
3-(5-Chloro-pyridin-2-yloxy)-8-pyridin-3-ylmethyl-8-aza-bicyclo[3.2.1]octane;
3-(3,4-Dichloro-phenoxy)-8-aza-bicyclo[3.2.1]octane-8-carbaldehyde;
3-(3,4-Dichloro-phenoxy)-8-pyridin-4-ylmethyl-8-aza-bicyclo[3.2.1]octane;
3-(5-Chloro-pyridin-2-yloxy)-8-aza-bicyclo[3.2.1]octane-8-carbaldehyde;
3-(5-Chloro-pyridin-2-yloxy)-8-pyridin-4-ylmethyl-8-bicyclo[3.2.1]octane;
8-Benzyl-3-(3,4-dichloro-phenoxy)-8-aza-bicyclo[3.2.1]octane;
2-[3-(6-Bromo-pyridin-2-yloxy)-8-aza-bicyclo[3.2.1]oct-8-yl]-acetamide;
2-[3-(3,4-Dichloro-phenoxy)-8-aza-bicyclo[3.2.1]oct-8-yl]-1H-benzimidazole;
[3-(3,4-Dichloro-phenoxy)-8-aza-bicyclo[3.2.1]oct-8-yl]-acetic acid ethyl ester;
3-(3,4-Dichloro-phenoxy)-8-(1H-tetrazol-5-ylmethyl)-8-aza-bicyclo[3.2.1]octane;
2-[3-(5-Chloro-pyridin-2-yloxy)-8-aza-bicyclo[3.2.1]oct-8-yl]-acetamide;
3-(3,4-Dichloro-phenoxy)-8-aza-phenethyl-8-aza-bicyclo[3.2.1]octane;
2-[3-(3,4-Dichloro-phenoxy)-8-aza-bicyclo[3.2.1]oct-8-yl]-thioacetamide;
3-(3,4-Dichloro-phenoxy)-8-(1-phenyl-ethyl)-8-aza-bicyclo[3.2.1]octane;
2-[3-(3,4-Dichloro-phenoxy)-8-aza-bicyclo[3.2.1]oct-8-yl]-1H-benzimidazole;
2-[3-(6-Methoxy-naphthalen-2-yloxy)-8-aza-bicyclo[3.2.1]oct-8-yl]-1H-benzimidazole;
3-(3,4-Dichloro-phenoxy)-8-(1-methyl-1H-tetrazol-5-ylmethyl)-8-aza-bicyclo[3.2.1]-octane;
3-(3,4-Dichloro-phenoxy)-8-thiazol-2-ylmethyl-8-aza-bicyclo[3.2.1]octane;
or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contain of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butdienyl; 1-, 2-, 3-, 4- or 5-hexenyl, or 1,3-hexdienyl, or 1,3,5-hextrienyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butdiynyl; 1-, 2-, 3-, 4-pentynyl, or 1,3-pentdiynyl; 1-, 2-, 3-, 4-, or 5-hexynyl, or 1,3-hexdiynyl or 1,3,5-hextriynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

Alkoxy is O-alkyl, wherein alkyl is as defined above.

Cycloalkoxy means O-cycloalkyl, wherein cycloalkyl is as defined above.

Cycloalkylalkyl means cycloalkyl as above and alkyl as above, meaning for example, cyclopropylmethyl.

Amino is $NH_2$ or NH-alkyl or N-(alkyl)$_2$, wherein alkyl is as defined above. In the context of this invention an aryl group designates a carbocyclic aromatic ring system such as phenyl, naphthyl (1-naphthyl or 2-naphthyl) or fluorenyl. The term aryl is also intended to cover a partially hydrogenated carbocyclic aromatic ring system, such as indanyl or 1,2,3,4-tetrahydronaphthyl.

In the context of this invention a heteroaryl group designates an aromatic mono- or bicyclic heterocyclic group, which holds one or more heteroatoms in its ring structure. Preferred heteroatoms include nitrogen (N), oxygen (O), and sulphur (S).

Preferred monocyclic heteroaryl groups of the invention include aromatic 5- and 6 membered heterocyclic monocyclic groups, including for example, but not limited to, oxazolyl (oxazol-2-yl, -4-yl, or -5-yl), isoxazolyl (isoxazol-3-yl, -4-yl, or -5-yl), thiazolyl (thiazol-2-yl, -4-yl, or -5-yl), isothiazolyl (isothiazol-3-yl, -4-yl, or -5-yl), tetrazolyl (1H-tetrazol-1-yl or -5-yl, 2H-tetrazol-2-yl or -5-yl or 5H-tetrazol-5-yl), 1,2,4-oxadiazolyl (1,2,4-oxadiazol-3-yl or -5-yl), 1,2,4-thiadiazolyl (1,2,4-thiadiazol-3-yl or -5-yl), 1,2,5-oxadiazolyl (1,2,5-oxadiazol-3-yl or-4-yl), 1,2,5-thiadiazolyl (1,2,5-thiadiazol-3-yl or -4-yl), imidazolyl (2-, 4-, or 5-imidazolyl), pyrrolyl (2- or 3-pyrrolyl), furanyl (2- or 3-furanyl), thienyl (2- or 3-thienyl), pyridyl (2-, 3- or 4-pyridyl), pyrimidyl (2-, 4-, 5- or 6-pyrimidyl), or pyridazinyl (3- or 4-pyridazinyl).

Preferred bicyclic heteroaryl groups of the invention include indolizinyl, in particular 2-, 5- or 6-indolizinyl; indolyl, in particular 2-, 5- or 6-indolyl; isoindolyl, in particular 2-, 5- or 6-isoindolyl; indazolyl, in particular 1- or 3-indazolyl; benzo[b]furanyl, in particular 2-, 5- or 6-benzofuranyl; benzo[b]thienyl, in particular 2-, 5- or 6-benzothienyl; benzimidazolyl, in particular 2-, 5- or 6-benzimidazolyl; benzoxazolyl, in particular 2-, 5- or 6-benzoxazolyl; benzothiazolyl, in particular 2-, 5- or 6-benzothiazolyl; benzoisothiazolyl (1,2-benzoisothiazolyl or 2,1-benzoisothiazolyl), in particular 1,2-benzoisothiazol-3-yl; purinyl, in particular 2- or 8-purinyl; quinolinyl, in particular 2-, 3-, 6-, 7- or 8-quinolinyl; isoquinolinyl, in particular 1-, 3-, 5-, 6- or 7-isoquinolinyl; cinnolinyl, in particular 6- or 7-cinnolinyl; phthalazinyl, in particular 6- or 7-phthalazinyl; quinazolinyl, in particular 2-, 6- or 7-quinazolinyl; quinoxalinyl, in particular 2- or 6-quinoxalinyl; 1,8-naphthyridinyl, in particular 1,8-naphthyridin-2-, 3-, 6- or 7-yl; pteridinyl, in particular 2-, 6- or 7-pteridinyl; and indenyl, in particular 1-, 2-, 3-, 5- or 5-indenyl.

Preferred polycyclic heteroaryl groups of the invention include dibenzofuranyl, in particular 2-dibenzofuranyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydro-chloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the sali-cylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may contain one or more chiral centers, and that such compounds exist in the form of isomers.

Moreover, the substituent —X—R$^b$ on position 3 of the 8-aza-bicyclo[3.2.1]octane skeleton of formula I may in particular be in the exo or endo configuration. In one embodiment of the invention the substituent at position 3 is in the exo configuration. In another embodiment of the invention the substituent at position 3 is in the endo configuration.

The invention includes all such isomers and any mixtures thereof including racemic mixtures.

Racemic forms can be resolved into the optical antipodes by known methods and techniques. One way of separating the isomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Labelled Compounds

The compounds of the invention may be used in their labelled or unlabeled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

Compounds of the invention may be tested for their ability to inhibit reuptake of the monoamines dopamine, noradrenaline and serotonin in synaptosomes eg such as described in WO 97/30997. Based on the balanced activity observed in these tests the compound of the invention is considered useful for the treatment the treatment, prevention or alleviation of a disease or a disorder or a condition of a mammal, including a human, which disease, disorder or condition is responsive to inhibition of monoamine neurotransmitter re-uptake in the central nervous system.

In a special embodiment, the compounds of the invention are considered useful for the treatment, prevention or alleviation of: mood disorder, depression, atypical depression, major depressive disorder, dysthymic disorder, bipolar disorder, bipolar I disorder, bipolar II disorder, cyclothymic disorder, mood disorder due to a general medical condition, substance-induced mood disorder, pseudodementia, Ganser's syndrome, obsessive compulsive disorder, panic disorder, panic disorder without agoraphobia, panic disorder with agoraphobia, agoraphobia without history of panic disorder, panic attack, memory deficits, memory loss, attention deficit hyperactivity disorder, obesity, anxiety, generalized anxiety disorder, eating disorder, Parkinson's disease, parkinsonism, dementia, dementia of aging, senile dementia, Alzheimer's disease, acquired immunodeficiency syndrome dementia complex, memory dysfunction in aging, specific phobia, social phobia, social anxiety disorder, post-traumatic stress disorder, acute stress disorder, drug addiction, drug misuse, cocaine abuse, nicotine abuse, tobacco abuse, alcohol addiction, alcoholism, kleptomania, pain, chronic pain, inflammatory pain, neuropathic pan, migraine pain, tension-type headache, chronic tension-type headache, pain associated with depression, fibromyalgia, arthritis, osteoarthritis, rheumatoid arthritis, back pain, cancer pain, irritable bowel pain, irritable bowel syndrome, post-mastectomy pain syndrome (PMPS), post-operative pain, post-stroke pain, drug-induced neuropathy, diabetic neuropathy, sympathetically-maintained pain, trigeminal neuralgia, dental pain, myofacial pain, phantom-limb pain, bulimia, premenstrual syndrome, premenstrual dysphoric disorder, late luteal phase syndrome, post-traumatic syndrome, chronic fatigue syndrome, urinary incontinence, stress incontinence, urge incontinence, nocturnal incontinence, sexual dysfunction, premature ejaculation, erectile difficulty, erectile dysfunction, premature female orgasm, restless leg syndrome, periodic limb movement disorder, eating disorders, anorexia nervosa, sleep disorders, pervasive developmental disorders, autism, Asperger's disorder, Rett's disorder, childhood disintegrative disorder, learning disabilities, motor skills disorders, mutism, trichotillomania, narcolepsy, post-stroke depression, stroke-induced brain damage, stroke-induced neuronal damage or Gilles de la Tourettes disease. In a preferred embodiment, the compounds are considered useful for the treatment, prevention or alleviation of depression.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoro-methane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to inhibition of mono-amine neurotransmitter re-uptake in the central nervous system, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

General: All reactions involving air sensitive reagents or intermediates were performed under nitrogen and in anhydrous solvents. Magnesium sulphate was used as drying agent in the workup-procedures and solvents were evaporated under reduced pressure.

Example 1

[3-(3,4-Dichloro-phenoxy)-8-aza-bicyclo[3.2.1]oct-8-yl]-acetic acid ethyl ester fumarate 5 g of 3-(3,4-dichloro-phenoxy)-8-aza-bicyclo[3.2.1]octane in 75 ml of N,N-dimethylformamide was first added 1.8 ml of ethyl bromoacetate then 4.5 ml triethylamine. The reaction mixture was stirred overnight at room temperature, then poured into 200 ml of water. The mixture was extracted twice with 150 ml of diethyl ether, the organic phase was dried with sodium sulphate and evaporated into an oil. 5.5 g 94%. 1.5 g of the oil was dissolved in a mixture of ethyl acetate and methanol. The solution was added 0.5 g of fumaric acid and evaporated, the residue was triturated with diethyl ether. Yield 1.3 g 65% Mp. 127-130° C.

Similarly was made:

2-[3-(3,4-Dichloro-phenoxy)-8-aza-bicyclo[3.2.1]oct-8-yl]-acetamide fumarate. Mp. 177-179° C.
2-[3-(5-Chloro-pyridin-2-yloxy)-8-aza-bicyclo[3.2.1]oct-8-yl]-acetamide fumarate. Mp. 185-187° C.
2-[3-(6-Bromo-pyridin-2-yloxy)-8-aza-bicyclo[3.2.1]oct-8-yl]-acetamide fumarate. Mp. 144-147° C.
8-Benzyl-3-(3,4-dichloro-phenoxy)-8-aza-bicyclo[3.2.1]octane fumarate. Mp. 212-216° C.
3-(5-Chloro-pyridin-2-yloxy)-8-pyridin-4-ylmethyl-8-aza-bicyclo[3.2.1]octane fumarate. Mp. 178-181° C.
3-(3,4-Dichloro-phenoxy)-8-pyridin-4-ylmethyl-8-aza-bicyclo[3.2.1]octane fumarate. Mp. 164-166° C.
2-[3-(3,4-Dichloro-phenoxy)-8-aza-bicyclo[3.2.1]oct-8-yl]-1H-benzimidazole fumarate. Mp. Dec. >215° C.
3-(5-Chloro-pyridin-2-yloxy)-8-pyridin-3-ylmethyl-8-aza-bicyclo[3.2.1]octane fumarate. Mp. 187-189° C.
3-(5-Chloro-pyridin-2-yloxy)-8-pyridin-2-ylmethyl-8-aza-bicyclo[3.2.1]octane fumarate. Mp. 192-194° C.
3-(3,4-Dichloro-phenoxy)-8-pyridin-3-ylmethyl-8-aza-bicyclo[3.2.1]octane fumarate. Mp. 185-187° C.
3-(3,4-Dichloro-phenoxy)-8-pyridin-2-ylmethyl-8-aza-bicyclo[3.2.1]octane fumarate. Mp. 189-191° C.
3-(3,4-Dichloro-phenoxy)-8-aza-bicyclo[3.2.1]octane-8-carboxylic acid phenylamide. Mp. 205-207° C.
3-(3,4-Dichloro-phenoxy)-8-aza-phenethyl-8-aza-bicyclo[3.2.1]octane. Mp. 132-134° C.
2-[3-(3,4-Dichloro-phenoxy)-8-aza-bicyclo[3.2.1]oct-8-yl]-thioacetamide. Mp. 230-231° C.
3-(3,4-Dichloro-phenoxy)-8-(1-phenyl-ethyl)-8-aza-bicyclo[3.2.1]octane, Mp. 258-260° C.
2-[3-(3,4-Dichloro-phenoxy)-8-aza-bicyclo[3.2.1]oct-8-yl]-1H-benzimidazole. Mp. 262-264° C.
2-[3-(6-Methoxy-naphthalen-2-yloxy)-8-aza-bicyclo[3.2.1]oct-8-yl]-1H-benzimidazole. Mp. 280° C. Decomp.

Example 2

3-(5-Chloro-pyridin-2-yloxy)-8-aza-bicyclo[3.2.1]octane-8-carbaldehyde

To 10 ml of ethyl format was added 0.4 g of 3-(5-Chloro-pyridin-2-yloxy)-8-aza-bicyclo[3.2.1]octane, the mixture was heated at reflux for 48 hours and evaporated to dryness, crystallized from ethyl acetate petroleum ether. Yield 200 mg (53%), Mp. 112-114° C.

Similarly was made:

3-(3,4-Dichloro-phenoxy)-8-aza-bicyclo[3.2.1]octane-8-carbaldehyde. Mp. 125-126° C.

Example 3

3-(3,4-Dichloro-phenoxy)-8-(1H-tetrazol-5-ylmethyl)-8-aza-bicyclo[3.2.1]octane

To 1 g of [3-(3,4-dichloro-phenoxy)-8-aza-bicyclo[3.2.1]oct-8-yl]-acetonitrile in 25 ml anhydrous toluene was added 0.7 g of triethylamin hydrochloride and 0.3 g sodium azide. The reaction mixture was stirred at 60-62° C. for 5 days, the product precipitated from the mixture and was isolated by filtration. Yield 0.27 g (24%) Mp. 233-235° C. (sublimation).

Example 4

3-(3,4-Dichloro-phenoxy)-8-(1-methyl-1H-tetrazol-5-ylmethyl)-8-aza-bicyclo[3.2.1]octane 3-(3,4-Dichloro-phenoxy)-8-(1H-tetrazol-5-ylmethyl)-8-aza-bicyclo[3.2.1]octane (5 g) in 50 ml of N,N-dimethylformamide was added 3 ml of triethylamine and stirred under a nitrogen atmosphere. Iodomethane (2 ml) was added drop wise. The reaction mixture was stirred at room temperature overnight and poured into 100 ml of water. The mixture was extracted with diethyl ether, which was dried with magnesium sulphate and evaporated to an oil, the oil was triturated in dry diethyl ether. Yield 0.55 g (11%) Mp. 119-120° C.

Example 5

3-(3,4-Dichloro-phenoxy)-8-thiazol-2-ylmethyl-8-aza-bicyclo[3.2.1]octane

2-[3-(3,4-Dichloro-phenoxy)-8-aza-bicyclo[3.2.1]oct-8-yl]-thioacetamide (0.5 g) in 5 ml of acetic acid was added 0.13 g of 50% chloroacetaldehyde in water. The reaction mixture was stirred at reflux overnight and cooled to room temperature and poured into 50 ml of water. The mixture was extracted twice with dichloromethane. The organic phase was dried with magnesium sulphate and evaporated to and oil. The product was isolated by column chromatography with dichloromethane/methanol (9:1) with 1% ammonia as eluent, the product fractions was evaporated to dryness. Yield 0.1 g (19%). Mp. 123-124° C.

The invention claimed is:

1. An 8-aza-bicyclo[3,2,1]octane chemical compound of Formula I:

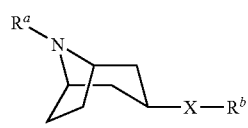

(I)

or any of its stereoisomers or any mixture of its stereoisomers, or a pharmaceutically acceptable salt thereof;

wherein $R^a$ represents —$(R^c)_n$—C(=O)R', —$(R^c)_n$—C(=O)OR', —$(R^c)_n$—C(=S)NR'R" or —$(R^c)_n$—C(=O)NR'R";

wherein $R^c$ represents alkyl;

n is 0 or 1;

R' and R" independent of each other represent hydrogen, alkyl, or aryl;

X represents —O—;

$R^b$ represents phenyl, pyridyl or naphthyl, which phenyl, pyridyl or naphthyl is substituted with one or more substituents independently selected from the group consisting of:

chloro, bromo and alkoxy.

2. The chemical compound of claim 1, or any of its stereoisomers or any mixture of its stereoisomers, or a pharmaceutically acceptable salt thereof, wherein $R^a$ represents —$(R^c)_n$—C(=O)R';

wherein R' represents hydrogen.

3. The chemical compound of claim 1, or any of its stereoisomers or any mixture of its stereoisomers, or a pharmaceutically acceptable salt thereof, wherein
$R^a$ represents —$(R^c)_n$—C(=O)OR';
wherein R' represents alkyl.

4. The chemical compound of claim 1, or any of its stereoisomers or any mixture of its stereoisomers, or a pharmaceutically acceptable salt thereof, wherein
$R^a$ represents —$(R^c)_n$—C(=S)NR'R";
wherein R' and R" represent hydrogen.

5. The chemical compound of claim 1, or any of its stereoisomers or any mixture of its stereoisomers, or a pharmaceutically acceptable salt thereof, wherein
$R^a$ represents —$(R^c)_n$—C(=O)NR'R";
wherein R' represents hydrogen; and
R" represents hydrogen or phenyl.

6. The chemical compound of claim 1, or any of its stereoisomers or any mixture of its stereoisomers, or a pharmaceutically acceptable salt thereof, wherein
n is 0.

7. The chemical compound of claim 1, or any of its stereoisomers or any mixture of its stereoisomers, or a pharmaceutically acceptable salt thereof, wherein
n is 1 and $R^c$ represents —CH$_2$—, —CH$_2$—CH$_2$— or —C(CH$_3$)H—.

8. The chemical compounds of claim 1, or any of its stereoisomers or any mixture of its stereoisomers, or a pharmaceutically acceptable salt thereof, wherein
$R^b$ represents phenyl or pyridyl substituted with one or more chloro.

9. The chemical compound of claim 1, or any of its stereoisomers or any mixture of its stereoisomers, or a pharmaceutically acceptable salt thereof, wherein
$R^b$ represents phenyl substituted with one or more chloro.

10. The chemical compound of claim 1, or any of its stereoisomers or any mixture of its stereoisomers, or a pharmaceutically acceptable salt thereof, wherein
$R^b$ represents pyridyl substituted with one or more chloro.

11. The chemical compound of claim 1, which is
2-[3-(3,4-Dichloro-phenoxy)-8-aza-bicyclo[3.2.1]oct-8-yl]-acetamide;
3-(3,4-Dichloro-phenoxy)-8-aza-bicyclo[3.2.1]octane-8-carboxylic acid phenylamide;
3-(3,4-Dichloro-phenoxy)-8-aza-bicyclo[3.2.1]octane-8-carbaldehyde;
3-(5-Chloro-pyridin-2-yloxy)-8-aza-bicyclo[3.2.1]octane-8-carbaldehyde;
2-[3-(6-Bromo-pyridin-2-yloxy)-8-aza-bicyclo[3.2.1]oct-8-yl]-acetamide;
[3-(3,4-Dichloro-phenoxy)-8-aza-bicyclo[3.2.1]oct-8-yl]-acetic acid ethyl ester;
2-[3-(5-Chloro-pyridin-2-yloxy)-8-aza-bicyclo[3.2.1]oct-8-yl]acetamide; or
2-[3-(3,4-Dichloro-phenoxy)-8-aza-bicyclo[3.2.1]oct-8-yl]-thioacetamide;
or any of its stereoisomers or any mixture of its stereoisomers, or a pharmaceutically acceptable salt thereof.

12. A pharmaceutical composition, comprising a therapeutically effective amount of a compound of claim 1, or any of its stereoisomers or any mixture of its stereoisomers, or a pharmaceutically acceptable salt thereof, together with at least one pharmaceutically acceptable carrier, excipient or diluent.

* * * * *